United States Patent [19]

Chéry

[11] 4,219,734
[45] Aug. 26, 1980

[54] X-RAY APPARATUS FOR TRANSVERSE AXIAL TOMOGRAPHY

[75] Inventor: Marc Chéry, Paris, France
[73] Assignee: Compagnie Generale de Radiologie, Paris, France
[21] Appl. No.: 928,217
[22] Filed: Jul. 26, 1978
[30] Foreign Application Priority Data
Jul. 29, 1977 [FR] France ................. 77 23445
[51] Int. Cl.² ............... A61B 6/00; A61B 6/02; H05G 1/02
[52] U.S. Cl. ................. 250/445 T; 250/513
[58] Field of Search .............. 250/445 T, 513
[56] References Cited

U.S. PATENT DOCUMENTS

| | | | |
|---|---|---|---|
| 2,667,588 | 1/1954 | Oswald | 250/513 |
| 3,091,696 | 5/1963 | Peyser | 250/513 |
| 3,829,701 | 8/1974 | Hura | 250/513 |
| 4,128,767 | 12/1978 | Stödberg | 250/513 |

*Primary Examiner*—Alfred E. Smith
*Assistant Examiner*—T. N. Grigsby
*Attorney, Agent, or Firm*—Edwin E. Greigg

[57] ABSTRACT

An X-ray apparatus for transverse axial tomography by direct exposure of a photographic film.

A localizer, constituted mainly by a lead-lined cylindrical tube, is fixed to a pivotal lever in the vicinity of the source of X-rays. It contains, in particular, a set of movable filters and movable opaque shutters each of which is moved by driving means according to the movements of the pivotal lever so that the essential part of the beam never impinges directly on the cassette holder and the rays located at the edge of the beam are less powerful than those located in the center region.

A transverse tomography apparatus of general utility.

6 Claims, 4 Drawing Figures

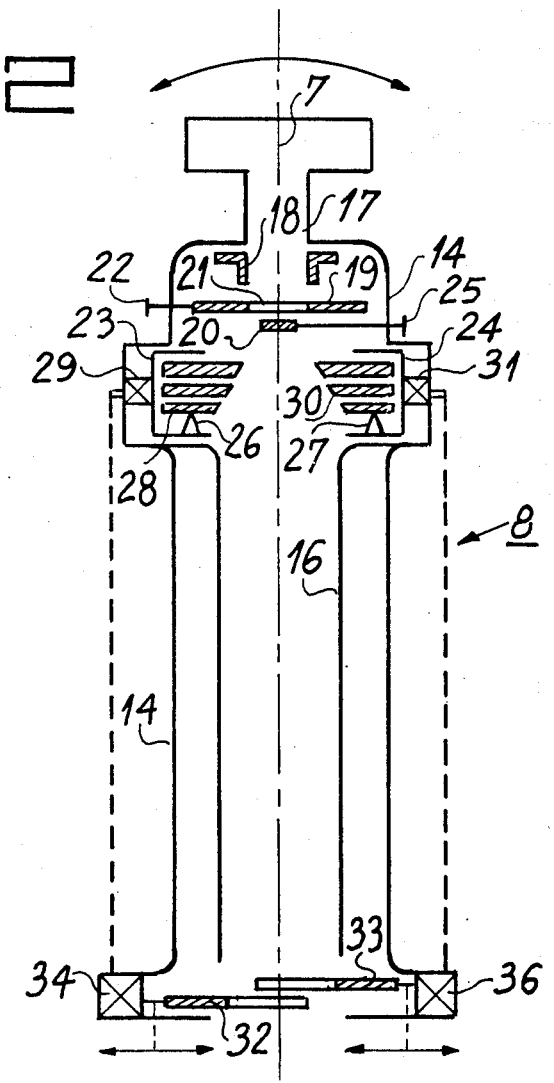
Fig_2
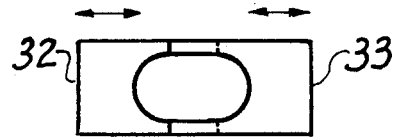
Fig_3

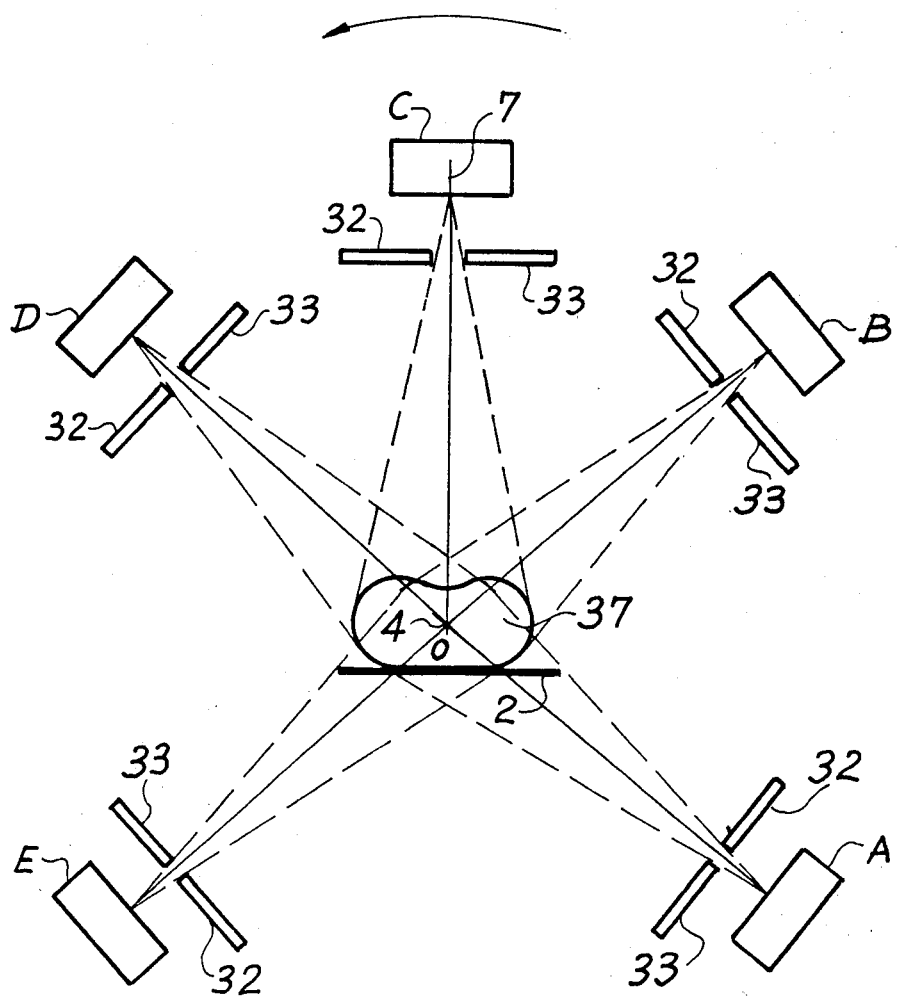
Fig_4

X-RAY APPARATUS FOR TRANSVERSE AXIAL TOMOGRAPHY

The invention relates to an X-ray apparatus for transverse axial tomography by a direct exposure of a photographic film.

Such apparatus comprise an examination table, a frame supporting a pivotal lever at the end of which is fixed a cassette support which undergoes a movement of trnaslation and rotation combined with the pivoting of the lever, and a source of X-rays emitting a beam in the direction of the cassette and through the examination table, said beam making an angle of about 20° with the normal to the table.

The pictures obtained with this type of apparatus often are of poor quality, in particular if the part of the picture concerning the organ to be studied is relatively distinct, the rest of the picture is most often overexposed and thus renders it impossible to exactly locate the position of the organ with respect to noteworthy points which should have been appeared in the picture.

The main object of the invention is to provide an apparatus which gives distinct pictures throughout their area.

The defects of the pictures are due, first to the fact that, the edges of the beam go beyond, in the course of the pivoting of the lever, the edges of the body to be examined and produce a marked overexposure of the photographic emulsion at this moment. This occurs principally when the body to be examined is not cylindrical, which is the case of a section of the human body with may be likened to an ellipse.

Further, even if it is arranged that the edges of the beam do not impinge on the film directly, the permeability of the body to be examined to the rays is much higher on the periphery of the section than in its centre part, since the thickness of the tissue travelled through diminished with increase in the distance to the centre of the section, which results in an overexposure of the periphery of the picture.

In the apparatus according to the invention, allowing the edges of the beam to impinge directly on the photographic film is avoided by modifying the opening of the beam in the course of the rotation of the pivotal lever and by adapting it to the shape of the body to be examined.

Lastly, in the case where the body to be examined has in its centre zone an osseous structure, the difference of exposure is still greater between the centre part and the periphery of the picture.

The overexposure of the peripheral zones of the picture is avoided by attenuating the intensity of the rays located at the periphery of the beam, and the difference of exposure between osseous tissues located at the centre and soft tissues is diminished by giving a shorter wavelength to the centre zone of the beam which enables it to pass through the osseous structure more easily.

The invention provides an X-ray apparatus for tomography, wherein a localizer is fixed at the source, said localizer containing in particular two movable filter holders provided with filtering plates and a set of opaque movable shutters, the filter holder and opaque shutters being controlled by driving means connected to the pivotal lever, the relative displacements of the filter holder and opaque shutters relative to the beam being homothetic relative to the source of rays.

As the lever rotates, the opening of the beam is adapted to the apparent dimension of the body to be X-rayed while the rays located at the periphery of the beam are weakened by the filters.

A better understanding of the invention will be had, and other features will be apparent, from the ensuing description of one embodiment with reference to the accompanying drawings in which:

FIG. 2 represents a diagrammatic sectional view to the localizer;

FIG. 3 represents a view of the opaque shutters;

FIG. 4 represents a diagram explaining the displacements of the shutters and the filters.

Figure 1:
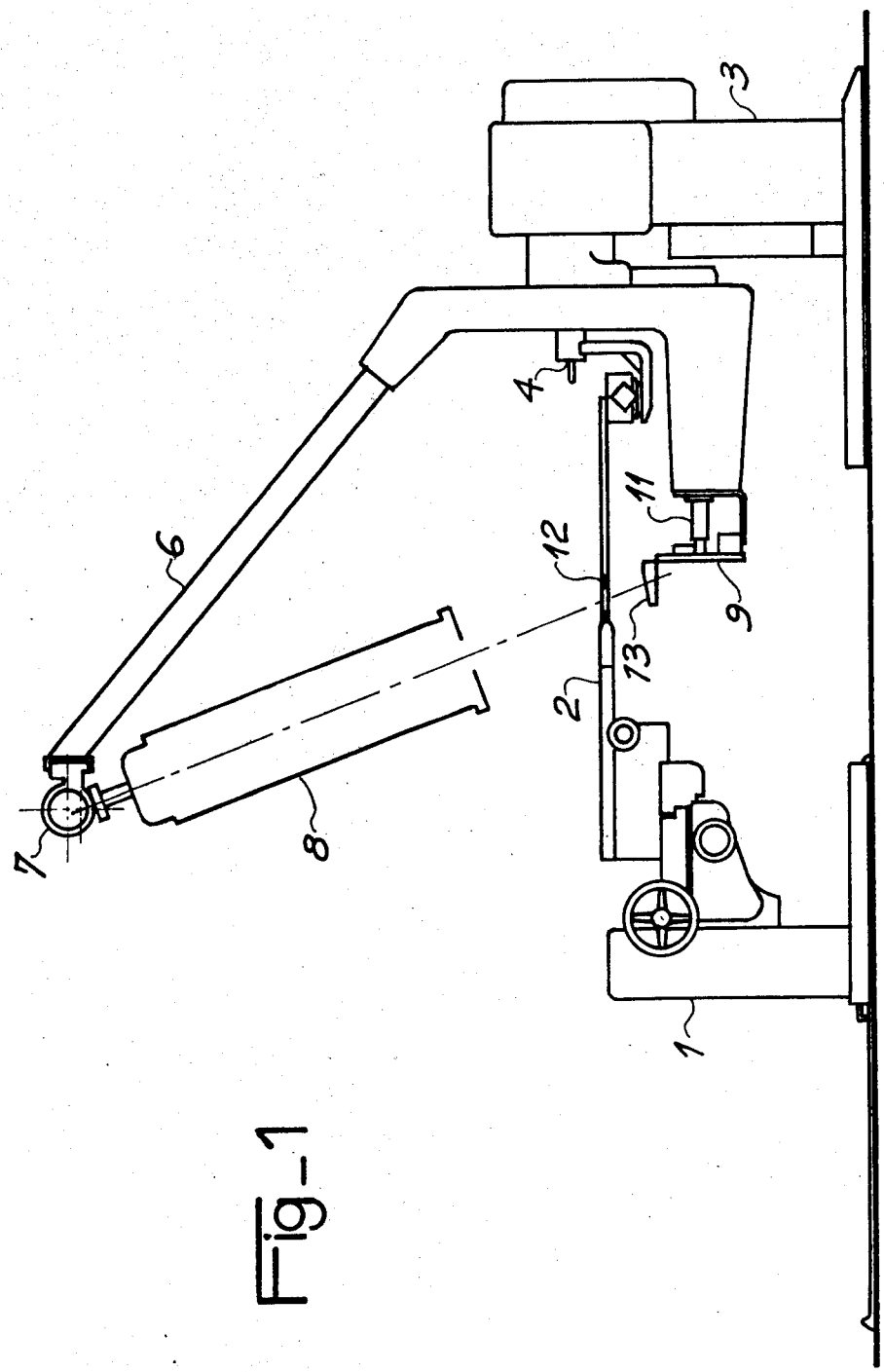
FIG. 1 represents a vertical sectional view of the assembly of the apparatus according to the invention.

The apparatus shown in FIG. 1 comprises a support 1, an examination table 2 and a frame 3 carrying a fixed shaft 4 around which a lever 6 is pivotable. Fixed at the upper end of the lever are the source 7 and the localizer 8 and, at the lower end, a cassette 9 mounted vertically on a shaft 11.

The latter is connected in the known manner to the frame 3 so as to remain rotationally stationary relative to the source of radiation in the course of the rotation of the lever 6 about the shaft 4. The source 7 emits a beam of X-rays in the direction of the cassette holder 9 by passing through the table 2 in a region 12 which is permeable to the X-rays, the angle of the beam relative to the normal to the table being about 20°. An antidiffusion grid 13 normal to the beam has, in the known manner, a variable permeability to the X-rays so as to compensate for the obliqueness of the beam with respect to the plane of the film.

FIG. 2 is a diagrammatic sectional view of the localizer 8 which is fixed, in the same way as the source 7, at the end of the pivotal lever 6. It comprises a case 14 containing a tube 16 lined with a thin layer of lead. Located against the source 7 is, first, a window 17 for limiting the format, comprising a sleeve 18 the inner walls of which are lead lined. A lead screen 19 comprising an elliptical aperture 21 is laterally movable in slideways (not shown) by a manual device 22 which also serves to lock it in position. This screen enables the beam to be precisely centred with the focal spot of the X-ray source.

A filter 20 is laterally movable on slideways (not shown) under the effect of a manual device 25 which also serves to lock it in position. This filter 20 is formed for an osseous tissue of average opacity by a copper sheet having a thickness of 0.1 mm. The dimension of this filter 20 approximately corresponds to the centre part of the beam which impinges on the osseous tissue. Once placed in position, it is secured relative to the case 14.

Two filter holders 23 and 24 are transversely slidable relative to the beam. They comprise manually accessible fixing devices 26 and 27 for immobilizing filter plates 28 and 30. Three filters have been shown in the filter holder, but it must be understood that their number, their thickness and their type may vary so as to present the desired coefficient of absorption, as will be explained hereinafter. The ends of the filters adjacent the beam are bevelled so that the absorption of the rays is progressive between the centre and the periphery of the beam. The displacements of the filter holders 23,24 are controlled respectively by driving means diagrammatically represented at 29 and 31.

The lower end of the localizer 8 is located as near as possible to the body to be examined without, however, hindering its positioning. Fixed at this end are movable shutters 32 and 33, the shape of which is shown in FIG. 3. These shutters are of lead and opaque to the rays. They are easily slidable while being guided by their U-shape. They are shifted by driving means diagrammatically represented at 34 and 36. The driving means 29 and 34, on one hand, and 31 and 36, on the other, comprise synchronous motors with speed reducers interconnected as indicated by the dotted lines in FIG. 2. The ratio of the speed reductions is such that the displacements of the shutters and filters are homothetic relative to the focal spot of the X-ray source.

It can be seen that with such an arrangement, the opening of the beam, controlled by the position of the shutters 32 and 33, is not only variable but variable in an asymmetrical manner according to the independent movements of the shutters.

Moreover, irrespective of the opening of the beam and its mean direction with respect to the lever, the centre part, unfiltered by the filters 28 and 30, is more intense than the peripheral parts which have passed through these filters.

However, when the body to be examined has on osseous structure in its centre zone, the filter 20 imparts to the corresponding parts of the beam a shorter wavelength which enables is to pass through the osseous tissue more easily; this results in a decrease in the difference of exposure between the centre osseous tissues and the peripheral soft tissues.

FIG. 4 explains the relative movements of the shutters 32 and 33 and filters 28, 30 relative to those of the pivotal lever 6 in the case where the major axis of the ellipse of the body to be examined is horizontal, the filter 20 remaining fixed in position. The body 37 is placed on the examination table 2. The axis of rotation (4) of the pivotal lever intersects the body 37 at 0 slightly in its upper part. The lever 6 moves from the lower right position A and reaches the lower left position E in following the direction indicated by the arrow and in passing through the intermediate positions B, C and D. The section of the body 37 is substantially elliptical. It can be seen that, for the positions 0A and 0E, the opening of the beam should be restricted toward the upper part of the table which is the solde concerned so that no ray is liable to directly reach the film in passing on one side of the body 37. It can be seen that the shutters, namely 32 when the pivotal lever is at A, and 33 when the lever is at E, are nearer to the axis of the beam than when the lever is at C in which the source sees the ellipse of the body 37 on its major axis. When the lever 6 leaves the position A, the shutter 32 is in a position nearer to the beam. When the lever reaches the position B, the shutter 32 starts to move away from the beam and reaches its withdrawn position at C. At this moment, the shutter 33 starts to move toward the axis of the beam and it must reach is more closed position when the lever is at D.

The pivotal lever 6 rotates about its shaft at a constant speed. In practise, the angles "AOB" and "DOE" are equal and in the neighborhood of 50°. The relative position of the filters at C, on the one hand, and at A and E, on the other, consequently depends solely on the speed at which they are displaced.

The use of this apparatus requires the determination of a number of parameters among which are the voltage of the source, the initial position of the filters and movable shutters, their speed of displacement, the composition and the number of the filters. This determination depends on the characteristics of the plane to be X-rayed and on the subject to be examined (mean permeability of the subject in the plane to be X-rayed which depends on the nature of the tissues and of the proportion of hard tissues and soft tissues, dimensions of the sections of the subject and osseous tissues), and requires the use of tables and even of a computer to achieve a rapid and reliable operation. The results obtained with this apparatus are remarkable. The uniformity of the exposure of the picture provides high distinction and high precision throughout its area and permits an easy measurement of the dimension of an organ and its location relative to the contours of the examined body and of the osseous tissues when these are present.

The large size of the localizer constitutes a practically absolute protection against diffused rays. The possibility of stacking a plurality of filter plates of various thicknesses and characteristics enables the value of the absorption of the filters to be set with precision.

I claim:

1. An X-ray apparatus for transverse axial tomography, comprising an examination table, a frame supporting a pivotal lever at one end of which is fixed a cassette holder to which is imparted a movement of rotation relative to the pivoting of the lever, a source of X-rays mounted at the other end of the lever and emitting a beam in the direction of the cassette, a window for limiting the format of the beam in the vicinity of the source, a variable diaphragm constituted by movable opaque shutters, the position of said shutters being controlled by first driving means so as to control the spread angle of the beam in dependence of the pivotal lever position, and further comprising two movable filters each formed by a filter holder provided with filtering plates and controlled by second driving means coupled to said first driving means in such manner that the relative displacements of the filter holders and the opaque shutters with respect to the beam are homothetic relative to the focal spot of the X-ray source.

2. An X-ray apparatus as claimed in claim 1, wherein the ends of the filtering plates adjacent the beam are bevelled.

3. An X-ray apparatus as claimed in claim 1, for X-raying a body having substantially an osseous structure at its centre, wherein there is provided a fixed detachable filter located substantially at the centre of the beam, the dimension of said fixed filter substantially corresponding to the dimension of the osseous structure.

4. An X-ray apparatus as claimed in claim 1, wherein the beam format limiting window, the movable filters and the movable opaque shutters are mounted inside a localizer fixed to the source of X-rays.

5. An X-ray apparatus as claimed in claim 1, wherein the filtering plates are substantially rectangular and have a thickness and a permeability to the rays which are variable from one plate to the other, the filter holders being so arranged as to contain a plurality of said plates at a time.

6. An X-ray apparatus as claimed in claim 1, further comprising between the beam format limiting window and the movable filters a transversely movable centering window.

* * * * *